United States Patent
Schmotzer

[11] Patent Number: 6,165,221
[45] Date of Patent: Dec. 26, 2000

[54] IMPLANT

[75] Inventor: Hans Schmotzer, Aarau, Switzerland

[73] Assignee: Plus Endoprothetik AG, Rotkreuz, Switzerland

[21] Appl. No.: 09/308,457

[22] PCT Filed: Nov. 14, 1997

[86] PCT No.: PCT/EP97/06377

§ 371 Date: Jul. 19, 1999

§ 102(e) Date: Jul. 19, 1999

[87] PCT Pub. No.: WO98/20817

PCT Pub. Date: May 22, 1998

[30] Foreign Application Priority Data

Nov. 14, 1996 [DE] Germany .......................... 196 47 155

[51] Int. Cl.[7] ...................................................... A61F 2/38
[52] U.S. Cl. ...................................................... 623/20.11
[58] Field of Search ............................. 623/16.11, 18.11, 623/20.14, 20.18, 20.21, 20.3, 20.31, 20.32, 22.11, 23.11

[56] References Cited

U.S. PATENT DOCUMENTS

| | | | |
|---|---|---|---|
| 3,924,277 | 12/1975 | Freeman et al. | 623/20 |
| 4,822,362 | 4/1989 | Walker et al. . | |
| 4,938,769 | 7/1990 | Shaw . | |
| 5,176,711 | 1/1993 | Grimes . | |
| 5,192,329 | 3/1993 | Christie et al. . | |
| 5,201,768 | 4/1993 | Caspari et al. | 623/20 |
| 5,207,711 | 5/1993 | Caspari et al. | 623/20 |
| 5,314,482 | 5/1994 | Goodfellow et al. | 623/20 |
| 5,326,368 | 7/1994 | Collazo . | |
| 5,336,266 | 8/1994 | Caspari et al. | 623/20 |
| 5,356,414 | 10/1994 | Cohen et al. . | |
| 5,413,605 | 5/1995 | Ashby et al. . | |
| 5,571,198 | 11/1996 | Drucker et al. . | |
| 5,935,173 | 8/1999 | Roger et al. | 623/20 |
| 5,997,577 | 12/1999 | Herrington et al. | 623/20 |
| 6,005,018 | 12/1999 | Cicierega et al. | 623/18 |

FOREIGN PATENT DOCUMENTS

| | | | |
|---|---|---|---|
| 0 303 006 | 2/1989 | European Pat. Off. . | |
| 0 380 045 | 8/1990 | European Pat. Off. . | |
| 0384854 | 8/1990 | European Pat. Off. | 623/20 |
| 0 551 791 | 7/1993 | European Pat. Off. . | |
| 0 552 949 | 7/1993 | European Pat. Off. . | |
| 0 552 950 | 7/1993 | European Pat. Off. . | |
| 0 612 509 | 8/1994 | European Pat. Off. . | |
| 611 559 | 8/1994 | European Pat. Off. . | |
| 0 636 353 | 2/1995 | European Pat. Off. . | |
| 0 709 074 | 5/1996 | European Pat. Off. . | |
| 0 709 075 | 5/1996 | European Pat. Off. . | |
| 2 700 263 | 7/1994 | France . | |
| 2 715 556 | 8/1995 | France . | |
| 28 02 655 | 8/1978 | Germany . | |
| 30 13 155 | 10/1980 | Germany . | |
| 32 05 526 | 9/1983 | Germany . | |
| 42 11 347 | 10/1993 | Germany . | |
| 42 301 18 | 3/1994 | Germany . | |
| 43 37 936 | 5/1995 | Germany . | |
| WO 92/15261 | 9/1992 | WIPO . | |
| WO 95/24874 | 9/1995 | WIPO . | |

*Primary Examiner*—Pedro Philogene
*Attorney, Agent, or Firm*—Knobbe, Martens, Olson & Bear, LLP

[57] ABSTRACT

An implant for placing on a plateau or resection surface of a joint bone includes at least one skidshaped cup having a joint seating surface, a ventral and a dorsal end. The joint seating surface extends in a longitudinal direction and has first and second curvature radii. The first curvature radius is transverse to the longitudinal direction and, at least in a coronal area, larger than the second curvature radius transverse to the longitudinal direction and in an area, which is loaded when the joint is fully bent. The first curvature radius continuously merges into the second curvature radius within a transitional area which extends over an angular range between about 30° and about 70°.

12 Claims, 4 Drawing Sheets

IMPLANT

FIELD OF THE INVENTION

The invention relates to an implant for placing on a plateau or resection surface of a joint bone.

BACKGROUND OF THE INVENTION

An implant of the aforementioned type is described in the DE 42 30 118 C2. This implant can replace at least a portion of the condyle surface of a femur bone. For this purpose, it comprises a femur cap which is mounted on the bone by means of a pin. The femur cup is seated on a prepared plateau surface of the bone.

In order to guarantee a secure hold of the implant on the bone, it must be ensured that the bone cement used for fixing the implant produces an as large as possible joining surface and enters into all cavities. To ensure this whilst only lightly pressing on the implant and to prevent bone cement or a flowing bone material from laterally oozing out over the cup, the latter is at its edge provided with a continuous circularly peripheral, archlike concave shape.

Other similar implants are described in EP 0 709 075 A1, EP 0 611 559 A1 and WO 95/24874.

However, all of the aforementioned implants do not solve the following problem. When a joint is stretched, the loaded joint seating surface between the implant and the associated joint base should be as large as possible, thus ensuring small surface pressure and good stability. Small surface pressure prevents, amongst other things, rapid wear of the artificial joint section.

A large seating surface is obtained in that a large curvature radius of the joint surface, or a small curvature, is selected in this area.

However, the desired large surface seating with a stretched joint offers the following disadvantage. If the implant is inserted transversely in such a manner that its longitudinal alignment does not coincide with the pivotal plane of the joint, then edge pressure may develop when bending the joint. This edge pressure makes excessive demands on both the joint base and the implant itself and causes rapid wear.

SUMMARY OF THE INVENTION

It is an object of the invention to further develop an implant of the aforementioned type in that surface pressure on the joint seating surface of the implant is kept low when the joint is stretched, whilst preventing edge pressure or incorrect loading of a joint during bending even with not exactly aligned implantation.

An aspect of the invention includes an implant for placing on a plateau or resection surface of a joint bone. The implant includes at least one skidshaped cup having a joint seating surface, a ventral and a dorsal end. The joint seating surface extends in a longitudinal direction and has first and second curvature radii. The first curvature radius is transverse to the longitudinal direction and, at least in a coronal area, larger than the second curvature radius transverse to the longitudinal direction and in an area, which is loaded when the joint is fully bent. The first curvature radius continuously merges into the second curvature radius within a transitional area which extends over an angular range between about 30° and about 70°.

Accordingly, the skidshaped cup comprises a joint seating surface the curvature radius of which transversely to its longitudinal extent is at least in the coronal area larger than its curvature radius transversely to its longitudinal extent in an area which is loaded when the joint is bent, and in a transitional area thereinbetween the larger curvature radius continuously merges into the smaller curvature radius.

A large seating surface of the implant in the joint base with the joint being stretched is ensured by the large curvature radius of the joint seating surface in the coronal area. Excessive wear is prevented and good stability of the joint is guaranteed.

If the joint is bent, then the curvature radius of the joint seating surface changes continuously at a point seated in the joint base, i.e. the large curvature radius merges into the smaller curvature radius. This allows prevention of edge pressure when bending the joint, even if an implant is not exactly inserted. Furthermore, freedom of movement for a respective joint, for example towards the side or relative to a rotation, can be increased.

A particularly preferred form of embodiment is characterised in that the transitional area extends over an angular range between approximately 30° and 70°, in particular between 40° and 60°. The transitional area should then not reach into the coronal area, as this would produce a reduced seating surface at this point. Furthermore, the joint seating surface with fully bent joint should be seated in the joint base with the smallest radius. The transitional area preferably begins for example with an implant replacing a section of a condyle surface with a femur bone approximately in the dorsal area of the skidshaped cup or somewhat offset in the direction of the coronal area.

According to a preferred form of embodiment, the skidshaped cup is at the one end which is facing away from the loaded seating surface with the joint bent off, pointed like a ships bow.

For improved anchorage of the implant in the bone, preferably at least one pin or means of this type is arranged at the side of the bone (for example at the proximal side). Equally, a central web can be provided at the side of the bone in the longitudinal direction extending from dorsal to ventral. This central web is accommodated in a complementary slot in the bone. This measure serves both a particularly exact alignment of the implant relative to the bone and stabilisation.

According to a particularly preferred form of embodiment, the skidshaped cup comprises an at least partially circular peripheral edge, and between the edges themselves or between the edges on the one hand and the central web on the other hand is/are provided one of more recesses, cutouts or pockets. Bone cement can enter these cutouts so that it will not ooze out over the edges when the implant is pressed onto the bone. Furthermore, due to suitable design of these pockets or cutouts, bone cement can be entered into all cavities when entering the implant. The central web can at the ends be pulled up to the respective peripheral edge of the cup.

If an implant is only required for a condyle surface, then it can be made of only one skidshaped cup which replaces a corresponding condyle surface. In this case, the implant is a uni-condyle slide.

If the condyle surfaces of two adjacent condyles are to be replaced by implant parts, then two at least essentially parallel skidshaped cups can be integrated or joined together with the implant. The implant is then a bi-condyle slide.

BRIEF DESCRIPTION OF THE DRAWINGS

The invention will now be described, also in view of further features and advantages, with reference to the enclosed drawings. The drawings show, in FIG. 1 a diagrammatical side view of an exemplary embodiment of an inventive implant in the form of a uni-condyle slide.

DETAILED DESCRIPTION OF THE INVENTION

Figure 1:
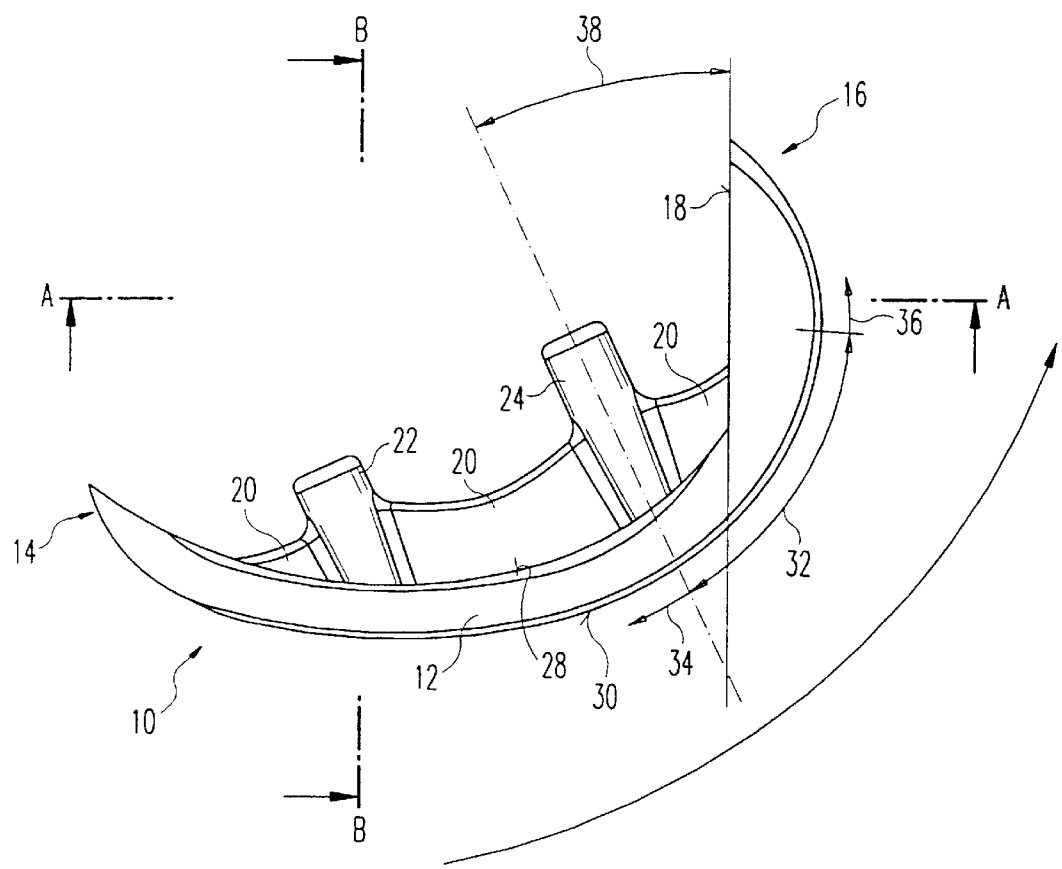

In FIGS. 1 to 7 is illustrated a form of embodiment of an implant 10 for replacement of a part of the condyle surface of a femur bone in the form of a uni-condyle slide.

Implant 10 covers a skidshaped cup 12 with a ventral 14 and a dorsal 16 end, and a dorsal intersecting surface 18 at the dorsal end 16 lies at an acute angle (double arrow 38) relative to the axes of pins 22, 24 (to be described later).

At the proximal side, at the side to be mounted to the joint bone (not illustrated), is provided a central web 20, which extends from the ventral 14 to the dorsal 16 end and runs in the longitudinal direction, in which are integrated the essentially parallel pins 22 and 24 which are spaced in the longitudinal direction. Central web 20 is divided into three sections by pins 22, 24. Naturally, alternatively only one pin or more than two pins can be provided.

Pins 22, 24 essentially serve stable mounting of the implant on the bone, for which a bone cement, for example autolog/homolog bone material, is used. As pins 22, 24 can be guided in a respective complementary bore in the bone, they additionally serve a correct alignment of implant 10.

Additional stabilisation, but also correct alignment, are also served by central web 20 which is accommodated and guided in a respectively shaped groove (not illustrated) in the bone. With an exactly formed groove in the bone, the longitudinal direction of implant 10 is accurately aligned in the pivotal plane of the joint.

In the described exemplary embodiment, central web 20 is on both ends respectively pulled up not quite to peripheral edges 28 of cup 12. Alternatively, central web 20 can also be fully pulled up.

Central web 20 together with the circularly peripheral pulled up peripheral edge 28 of cup 12 forms an at least partially peripheral cutout or pocket 26 in which bone cement is received when the implant is pushed towards the bone and spreads if possible into all cavities between implant and bone. In the present example, peripheral edge 28 is not in the form of a cutting edge.

At ventral end 14, skidshaped cup 12 is shaped like a ship's bow. But ends of different shape can also be chosen.

At the distal side of skidshaped cup 12 extends a joint seating surface 30 in the longitudinal direction of skidshaped cup 12. Joint seating surface 30 of an inserted implant 10 glides in a joint base (not illustrated), which is coated, for example with polyethylene.

Figure 2:
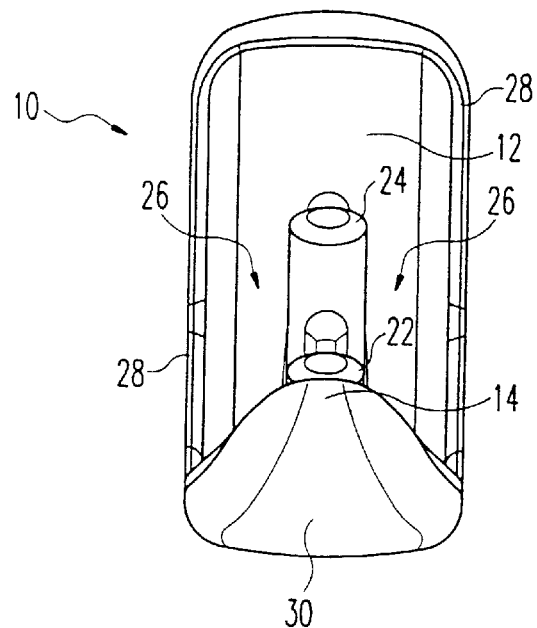
FIG. 2 a diagrammatical front view of the uni-condyle slide of FIG. 1.
Figure 3:
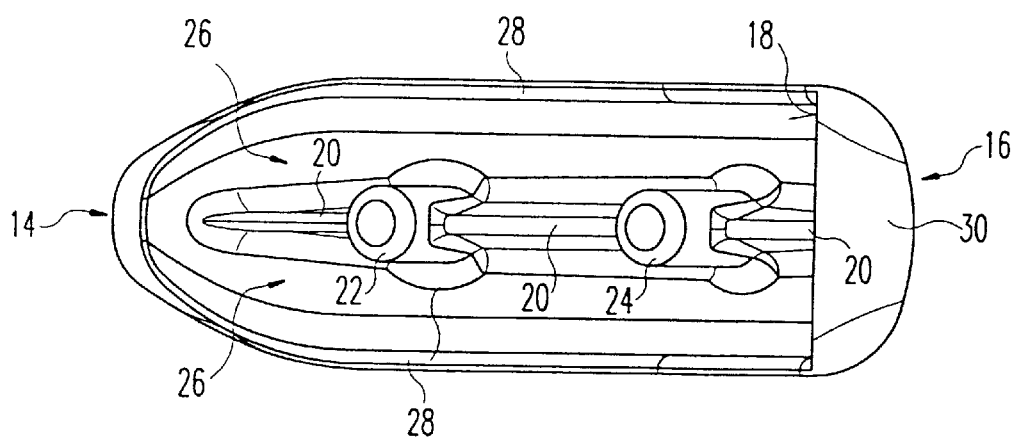
FIG. 3 a diagrammatical top view of the uni-condyle slide of FIG. 1.
Figure 4:
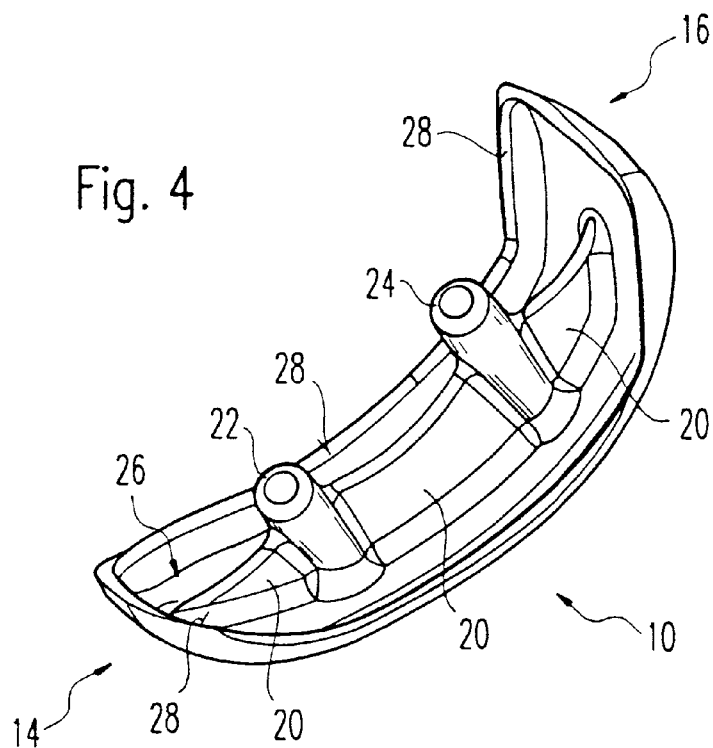
FIGS. 4 and 5 respective diagrammatical perspective views of the uni-condyle slide of FIG. 1.
Figure 5:
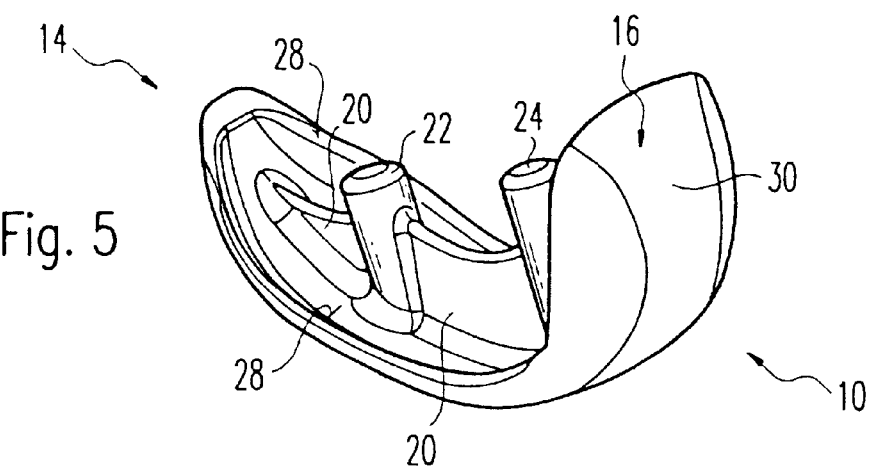

Joint seating surface 30 has transversely to its longitudinal extent at each point a defined curvature with a corresponding curvature radius and is at peripheral edges 28 which extend parallel to the longitudinal direction pulled upwards, as is particularly clearly shown in FIG. 2, thus establishing skid-shaped cup 12.

Figure 6:
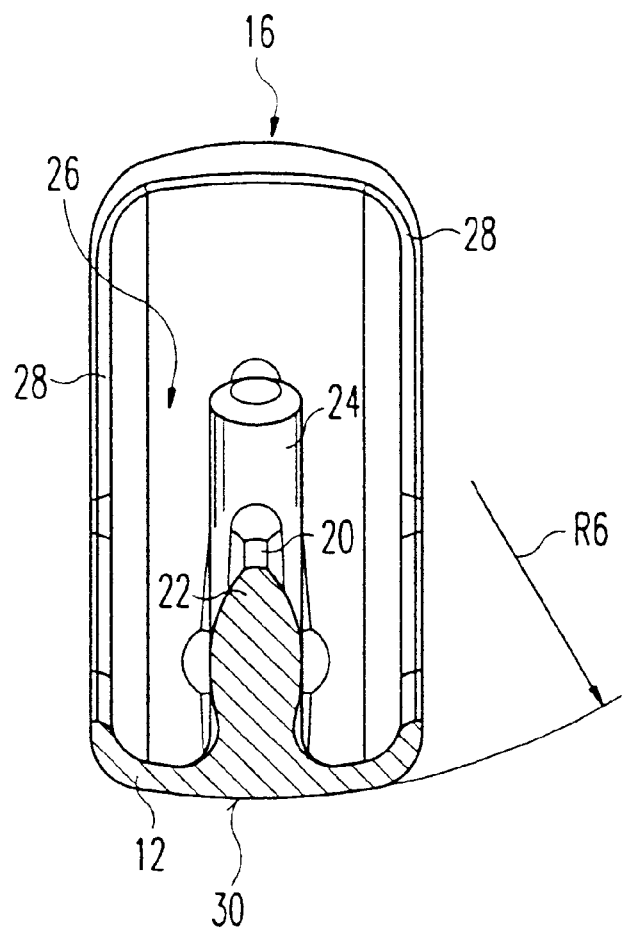
FIG. 6 a cross-sectional view of the uni-condyle slide of FIG. 1, cross-sectionally along line B—B in FIG. 1.
Figure 7:
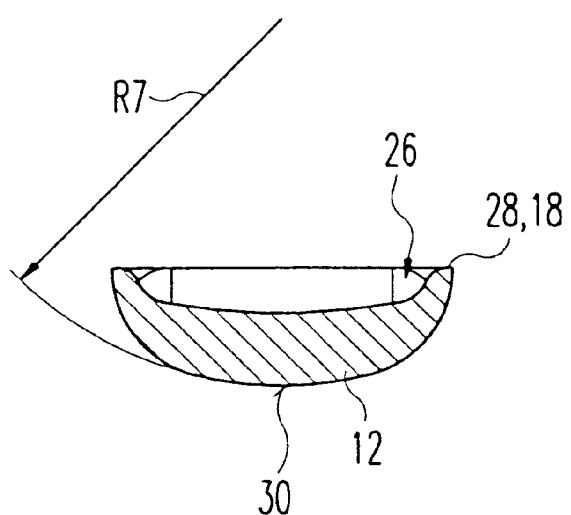
FIG. 7 a cross-sectional view of the uni-condyle slide of FIG. 1, cross-sectionally along line A—A in FIG. 1.

According to FIG. 6 (cross-section B—B of FIG. 1 in the coronal plane), curvature radius $R_6$ in the coronal area is chosen to be large, i.e. the curvature is relatively flat. This ensures a large seating surface between implant and complementary mounting surface of the associated joint base, which contributes to stability and low wear of the joint.

However, if the implant is inserted slightly transversely to the pivotal axis of the joint, then bending of the joint with the aforedescribed curvature radius can result in edge pressure. This would not only result in rapid wear of the joint but could also produce incorrect loads on bones and muscles by developing forces.

In order to avoid this effect, a smaller curvature radius $R_7$ (i.e. $R_6 > R_7$), i.e. a large curvature, is chosen in the dorsal area of the seating surface.

Between the two areas with radii $R_6$ and $R_7$ is provided a transitional area 32 (see FIG. 1), where both radii $R_6$ and $R_7$ continuously merge into each other.

Transitional area 32 of the present exemplary embodiment extends from slightly below the dorsal plane up to approximately the axis of pin 24. From there on up to the ventral end, the joint surface is set with radius $R_6$ (arrow 34). From the other end of transitional area 32 in the dorsal direction, joint seating surface 30 is set with curvature radius $R_7$ (arrow 36).

In all, when bending a not exactly inserted implant 10, skidshaped cup 12 can glide unimpeded in the joint base. Edge pressure is avoided. And yet, a large seating surface when the joint is stretched is ensured.

It is, of course, also possible to provide an implant with two skidshaped cups 12 which are essentially parallel relative to each other. This would then be a bi-condyle slide by means of which two condyle surfaces arranged alongside each other could be replaced. The two skidshaped cups could then be simply shaped in one part in an implant or they could be interconnected by a connecting element.

It is understood that the invention is not restricted to the present form of embodiment. The invention can be applied to any implant which is inserted in the joint area where a pivotal process takes place. In a state in which the joint is usually most severely loaded, a large seating surface is to be ensured, i.e. a small curvature or a large curvature radius of the joint seating surface.

However, no edge pressure is to develop when bending the joint, so that the curvature radius of the joint seating surface can reduce in the pivotal or bending direction, or the curvature can increase accordingly.

LIST OF REFERENCE MARKS

10—Implant (here: uni-condyle slide)
12—Skidshaped Cup
14—Ventral End
16—Dorsal End
18—Dorsal Intersecting Surface
20—Centre Web
22—Pin
24—Pin
26—Cutout, Pocket
28—Peripheral Edge
30—Joint Seating Surface
32—Transitional Area
34—Arrow $R_6$ 36—Arrow $R_7$
38—Acute Angle

What is claimed is:

1. An implant for placing on a plateau or resection surface of a joint bone, comprising:
at least one skidshaped cup having a joint seating surface, a ventral and a dorsal end, the joint seating surface extending in a longitudinal direction and having first and second curvature radii, the first curvature radius being transverse to the longitudinal direction and, at least in a coronal area, being larger than the second curvature radius transverse to the longitudinal direction and in an area, which is loaded when the joint is fully bent, wherein the first curvature radius continuously merges into the second curvature radius within a transitional area which extends over an angular range between about 30° and about 70°.

2. The implant of claim 1, wherein the transitional area extends over an angular range between about 40° and about 60°.

3. The implant of claim 1, wherein the transitional area starts in an area of the skidshaped cup which is loaded when the joint of fully bent.

4. The implant of claim 1, wherein the transitional area starts in an area which is slightly displaced in the direction of the coronal area.

5. The implant of claim 1, wherein the skidshaped cup is pointed at the ventral end facing away from the loaded joint seating surface when the joint is fully bent.

6. The implant of claim 1, wherein the skidshaped cup comprises at a side of the joint bone at least one pin which is insertable into the joint bone and mountable therein.

7. The implant of claim 1, wherein the skidshaped cup comprises at a side of the joint bone means for anchoring insertable into the bone and mountable therein.

8. The implant of claim 1, wherein the skidshaped cup comprises at a side of the joint bone a central web which extends at least from ventral to dorsal in the longitudinal direction.

9. The implant of claim 1, wherein the skidshaped cup comprises a circular peripheral edge, and at least one element selected from a group including pockets, cutouts and recesses within the circular peripheral edge.

10. The implant of claim 9, wherein the skidshaped cup comprises a circular peripheral edge, and at least one element selected from a group including pockets, cutouts and recesses between the circular peripheral edge and the central web.

11. The implant of claim 1, comprising a single skidshaped cup which serves as a uni-condyle slide.

12. The implant of claim 1, comprising two parallel skidshaped cups which form a bi-condyle slide.

* * * * *